(12) United States Patent
Nakagawa et al.

(10) Patent No.: US 12,312,464 B2
(45) Date of Patent: May 27, 2025

(54) CURING CATALYST USED FOR CURING OF POLYMER, MOISTURE CURABLE COMPOSITION, AND METHOD FOR PRODUCING CURED PRODUCT

(71) Applicant: NITTO KASEI CO., LTD., Osaka (JP)

(72) Inventors: Yuya Nakagawa, Osaka (JP); Yasuo Imakura, Osaka (JP)

(73) Assignee: NITTO KASEI CO., LTD., Osaka (JP)

( * ) Notice: Subject to any disclaimer, the term of this patent is extended or adjusted under 35 U.S.C. 154(b) by 569 days.

(21) Appl. No.: 17/779,052

(22) PCT Filed: Nov. 25, 2020

(86) PCT No.: PCT/JP2020/043854
§ 371 (c)(1),
(2) Date: May 23, 2022

(87) PCT Pub. No.: WO2021/106942
PCT Pub. Date: Jun. 3, 2021

(65) Prior Publication Data
US 2022/0411579 A1    Dec. 29, 2022

(30) Foreign Application Priority Data

Nov. 29, 2019 (JP) ................ 2019-216651

(51) Int. Cl.
| | | |
|---|---|---|
| *C08L 71/02* | (2006.01) | |
| *C08G 65/336* | (2006.01) | |
| *C08G 77/08* | (2006.01) | |
| *C08L 101/10* | (2006.01) | |

(52) U.S. Cl.
CPC ........... *C08L 71/02* (2013.01); *C08G 65/336* (2013.01); *C08G 77/08* (2013.01); *C08L 101/10* (2013.01)

(58) Field of Classification Search
CPC .................................................. C08G 77/08
See application file for complete search history.

(56) References Cited

U.S. PATENT DOCUMENTS

| | | |
|---|---|---|
| 4,546,017 A | 10/1985 | Flackett et al. |
| 2006/0199886 A1 | 9/2006 | Ryang |
| 2008/0076878 A1 | 3/2008 | Wakioka et al. |
| 2009/0163662 A1 | 6/2009 | Yasuda et al. |
| 2014/0193975 A1 | 7/2014 | Ogihara |
| 2016/0160081 A1 | 6/2016 | Klotzbach |

FOREIGN PATENT DOCUMENTS

| | | | | |
|---|---|---|---|---|
| CN | 1950459 A | 4/2007 | | |
| CN | 102766333 A | 11/2012 | | |
| CN | 109608639 A | 4/2019 | | |
| CN | 111875801 A | * 11/2020 | ............. | C08G 77/44 |
| JP | 60-161457 A | 8/1985 | | |
| JP | 63-42942 B2 | 8/1988 | | |
| JP | 8-41358 A | 2/1996 | | |
| JP | 2002-249672 A | 9/2002 | | |
| JP | 2003-064305 A | 3/2003 | | |
| JP | 2003-147220 A | 5/2003 | | |
| JP | 2005-320412 A | 11/2005 | | |
| JP | 5446265 B2 | 3/2014 | | |
| JP | 2014114434 A | * 6/2014 | | |
| JP | 2015-151381 A | 8/2015 | | |
| WO | WO-2005035622 A1 | * 4/2005 | .......... | B01J 31/0239 |
| WO | 2009/093348 A1 | 7/2009 | | |
| WO | WO2015/151788 A1 | 8/2015 | | |

OTHER PUBLICATIONS

Machine translation of CN 111875801 (no date).*
Machine translation of JP 2014-114434 (no date).*
International Search Report mailed Feb. 2, 2021, issued in corresponding International Application No. PCT/JP2020/043854, filed Nov. 25, 2020, 3 pages.
Notice of Reasons for Refusal mailed Sep. 7, 2021, issued in corresponding Japanese Application No. 2021-531416, 6 pages.
Notice of Reasons for Refusal mailed Nov. 24, 2021, issued in corresponding Japanese Application No. 2021-531416, 8 pages.
Notice of Reasons for Refusal mailed Feb. 8, 2022, issued in corresponding Japanese Application No. 2021-531416, 4 pages.
Extended European Search Report mailed Jan. 9, 2023, issued in corresponding International Application No. PCT/JP2020/043854, filed Nov. 25, 2020, 6 pages.
Chinese Office Action and machine translation thereof for CN 202080080625.7, mailed Sep. 27, 2023 (19 pages).

* cited by examiner

*Primary Examiner* — Marc S Zimmer
(74) *Attorney, Agent, or Firm* — CHRISTENSEN O'CONNOR JOHNSON KINDNESS PLLC

(57) ABSTRACT

When considering the prior art, the objective of the present invention is to provide a curing catalyst which is highly safe and has a curing rate suitable for practical use. According to the present invention, provided is a curing catalyst [B] which is used for curing a polymer [A] having a reactive hydrolyzable silicon-containing group, the curing catalyst [B] containing a metal alkoxide [B1] and an ammonium hydroxide [B2], wherein: the metal alkoxide [B1] includes one or both of a titanium compound [B1a] represented by chemical formula (1) and another metal alkoxide [B1b]; the another metal alkoxide [B1b] is an alkoxide of a metal other than titanium; and the ammonium hydroxide [B2] is represented by chemical formula (2).

6 Claims, No Drawings

CURING CATALYST USED FOR CURING OF POLYMER, MOISTURE CURABLE COMPOSITION, AND METHOD FOR PRODUCING CURED PRODUCT

TECHNICAL FIELD

The present invention relates to a curing catalyst used for curing a polymer, a moisture-curable composition, and a method for producing a cured product.

BACKGROUND ART

One-pack type moisture-curable rubber compositions generally have a high curing rate and do not require weighing and mixing of various additives such as a base polymer, a cross-linking agent and a catalyst before use, and therefore is superior in workability as compared with the two-part type.

As these one-pack type moisture-curable rubber compositions, silicone-based rubber, modified silicone-based rubber, urethane-based rubber, polysulfide-based rubber and the like are known.

Organopolysiloxane compositions are widely used as the one-pack type moisture-curable rubber composition of the silicone-based rubber, and cure at room temperature to form a rubber elastic body. Siloxane polymer compounds having a main chain of —Si—O— bonds obtained by crosslinking and polymerizing organosiloxanes are widely used in the fields of construction, civil engineering, electricity, electronics, automobile, etc. because of their excellent properties such as water repellency, heat resistance, weather resistance, cold resistance, and electrical insulation.

As the one-pack type moisture-curable rubber composition of modified silicone-based rubber, there is a composition containing a polymer having a polyether as a main chain and having a crosslinkable reactive hydrolyzable silicon functional group. The curable composition of this polymer has better storage stability, weather resistance, foaming resistance and discoloration resistance than those of the urethane-based rubber, and has better curability than that of the polysulfide-based rubber, and has little pollution to the surroundings and no toxicity.

It is considered that the reaction mechanism of the process in which the silicone-based rubber and the modified silicone-based rubber become a cured product is based on a condensation reaction or an addition reaction of a reactive hydrolyzable silicon-containing group in the presence of water, and the polymerization proceeds to form a cured polymer having a three-dimensional network structure. A curing catalyst is used to accelerate the curing process in this reaction (Patent Literature 1 to 5).

CITATION LIST

Patent Literature

Patent Literature 1: JPA1996-41358
Patent Literature 2: JPA1985-161457
Patent Literature 3: JPA1988-42942
Patent Literature 4: JPA2003-147220
Patent Literature 5: JPB5446265

SUMMARY OF INVENTION

Technical Problem

As a curing catalyst for the cured composition of the silicone-based rubber and modified silicone-based rubber having the reactive hydrolyzable silicon-containing group, tin carboxylate compounds, alkyltin salt compounds and the like have been used, but there are concerns about their effects on living organisms as endocrine disruptors. Therefore as a moisture-curable composition which does not use such substances, a combined catalyst of a carboxylic acid and an amine (Patent Literature 1) has been proposed. However, there is a problem that a sufficient curing speed cannot be obtained during operation.

In Patent Literature 2 and 3, the use of a titanium acid ester compound such as diisopropoxy titanium bis (alkyl acetoacetonate) as a catalyst has been proposed. However there is a problem that the compound is easily decomposed by moisture contained in additives and fillers in the composition, and the curing speed varies due to humidity during operation, so that a stable cured product cannot be obtained.

In Patent Literature 4, the use of a titanium tetracarboxylate compound as a catalyst has been proposed. In this case, however, a practical curing speed cannot be obtained.

In Patent Literature 5, the use of a quaternary ammonium salt as a catalyst has been proposed. In this case, however, a sufficient curing rate cannot be obtained during construction.

Therefore, it has been desired to develop a curing catalyst having a high safety (low toxicity and low environmental pollution) and a practical curing speed.

In view of the above-mentioned prior art, an object of the present invention is to provide a curing catalyst having a high safety and a practical curing speed.

Solution to Problem

An aspect of the present invention provides a curing catalyst [B] used for curing a polymer [A] having a reactive hydrolyzable silicon-containing group, wherein
the curing catalyst [B] contains a metal alkoxide [B1] and an ammonium hydroxide [B2], the metal alkoxide [B1] contains one or both of a titanium compound [B1a] represented by Chemical Formula (1) and another metal alkoxide [B1b], the another metal alkoxide [B1b] is an alkoxide of a metal other than titanium, the ammonium hydroxide [B2] is represented by Chemical Formula (2).

As a result of intensive investigation by the present inventors, it has been found that when a curing catalyst [B] containing a metal alkoxide [B1] and an ammonium hydroxide [B2] was used, the curing rate of the polymer [A] was significantly increased, thereby leading to completion of the present invention. Since this catalyst does not contain tin, it is highly safe and can be manufactured at low cost.

DESCRIPTION OF EMBODIMENTS

Hereinafter, the present invention will be explained in detail.

The curing catalyst [B] of the present invention is used for curing a polymer [A] having a reactive hydrolyzable silicon-containing group. The polymer [A] is preferably a liquid at room temperature.

1. Polymer [A]

The polymer [A] has at least one reactive hydrolyzable silicon-containing group per molecule at a molecular terminal or a side chain. The reactive hydrolyzable silicon-containing group may be present at the terminal of the polymer [A] molecule, may be present in the side chain, and may be present at both the terminal and the side chain. The number of reactive hydrolyzable silicon-containing groups may be at least one per molecule of the polymer [A], but from the viewpoint of the curing speed and physical properties of the cured product, it is preferable that the number is 1.5 or more per molecule on average. A known method can be adopted as a method of bonding the reactive hydrolyzable silicon-containing group to the main chain of the polymer.

The reactive hydrolyzable silicon-containing group is a group having a silicon atom bonded to a reactive group consisting of a hydrolyzable group (e.g. halogen, alkoxy, alkenyloxy, acyloxy, amino, aminooxy, oxime, amide) or a hydroxyl group, and has a property of causing a condensation reaction by using a catalyst or the like as necessary in the presence of moisture or a crosslinking agent. Specifically, examples of the reactive hydrolyzable silicon-containing group include a halogenated silyl group, an alkoxysilyl group, an alkenyloxysilyl group, an acyloxysilyl group, an aminosilyl group, an aminooxysilyl group, an oximesilyl group, and an amidesilyl group and the like.

The number of reactive hydrolyzable groups bonded to one silicon atom is selected from the range of 1 to 3. In addition, the reactive hydrolyzable group bonded to one silicon atom may be one or more kinds. Further, a reactive hydrolyzable group and a non-reactive hydrolyzable group may be bonded to one silicon atom, or a hydrolyzable group and a hydroxyl group may be bonded to one silicon atom. As the reactive hydrolyzable silicon-containing group, the alkoxysilyl group (including a monoalkoxysilyl group, a dialkoxysilyl group, and a trialkoxysilyl group) is particularly preferable in terms of easy handling.

Among the above-mentioned alkoxysilyl groups, the trialkoxysilyl group is preferred because it has high activity and provides good curability, and the resulting cured product has excellent resilience, durability and creep resistance. On the other hand, the dialkoxysilyl group and monoalkoxysilyl group are preferable because they have excellent storage stability and the resulting cured product has high elongation and high strength.

By using the polymer [A] in which the reactive hydrolyzable silicon-containing group is a dialkoxysilyl group in combination with the polymer [A] in which the reactive hydrolyzable silicon-containing group is a trialkoxysilyl group, the physical properties and curability of the cured product can be balanced.

Examples of the polymer [A] include an organic polymer [A1] and an organopolysiloxane [A2].

(Organic Polymer [A1])

The main chain of the organic polymer [A1] used in the present invention includes one having a carbon atom, for example, an alkylene oxide polymer, a polyester polymer, an ether/ester block copolymer, a polymer of ethylenically unsaturated compound, a polymer of diene-based compound and the like.

Examples of the alkylene oxide polymer include those having one or more kinds of repeating units such as

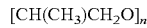

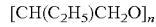

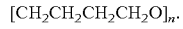

Here, n is the same or different and is an integer of 2 or more. These alkylene oxide polymers may be used alone or in combination of two or more kinds. Further, a copolymer containing two or more kinds of the above repeating units may also be used.

Examples of the polyester polymer include those having a carboxylic acid such as acetic acid, propionic acid, maleic acid, phthalic acid, citric acid, pyruvic acid, lactic acid, and an anhydride thereof, an intramolecular and/or intermolecular ester thereof and a substituted product thereof as a repeating unit.

Examples of the ether/ester block copolymer include those having both a repeating unit used in the above-described alkylene oxide polymer and a repeating unit used in the above-described polyester polymer as a repeating unit.

Further, Examples of the polymer of the ethylenically unsaturated compound and the diene-based compound include a homopolymer of ethylene, propylene, acrylate, methacrylate, vinyl acetate, acrylonitrile, styrene, isobutylene, butadiene, isoprene, or chloroprene and the like, and a copolymer of two or more of these compounds. More specifically, polybutadiene, styrene-butadiene copolymer, acrylonitrile-butadiene copolymer, ethylene-butadiene copolymer, ethylene-propylene copolymer, ethylene-vinyl acetate copolymer, ethylene-(meth) acrylate copolymer, polyisoprene, styrene-isoprene copolymer, isobutylene-isoprene copolymer, polychloroprene, styrene-chloroprene copolymer, acrylonitrile-chloroprene copolymer, polyisobutylene, polyacrylate, polymethacrylate and the like can be mentioned. These polymers may be used alone or in combination of two or more kinds.

As the organic polymer [A1], an organic polymer having a polar group such as a nitrogen-containing characteristic group in the molecule may also be used. Specific examples of the nitrogen-containing characteristic group include those represented by a (thio) urethane group, an allophanate group, a bonding group derived from a (thio) urethane group such as other N-substituted urethane groups and an N-substituted allophanate group, a (thio) urea group, a biuret group, other N-substituted urea groups, an N,N'-substituted urea group, a bonding group derived from a (thio) urea group such as an N-substituted biuret group and an N,N'-substituted biuret group, an amide group, a bonging group derived from an amide group such as an N-substituted amide group, a bonding group derived from an imino group, a (thio) ester group, a (thio) ether group and the like, but are not limited thereto. Among these groups, the nitrogen-containing characteristic group is preferable in terms of high curability, and the bonding group derived from a (thio) urethane group and the bonding group derived from a (thio) urea group are more preferable in terms of ease of synthesis. Further, only one nitrogen-containing characteristic group may be contained in the organic polymer [A1], and one or more kinds of a plurality of nitrogen-containing characteristic groups may be contained in the organic polymer [A1]. Here, the terms of "(thio)" and "N-substituted" are the same as above.

When the organic polymer [A1] contains a polar group such as the nitrogen-containing characteristic group, the toughness of the cured product is improved, and the curability and adhesive strength are increased. In particular, when the cross-linkable silicon group is linked to the main chain via a polar group such as the nitrogen-containing characteristic group, the curability is further improved. The reason for this is that the polar groups of the nitrogen-containing characteristic groups strongly attract each other due to an interaction such as a hydrogen bond. It is considered that when the polar groups of the nitrogen-containing characteristic groups strongly attract each other, the molecules of the curable resin also strongly bind to each other (form a domain), thereby exhibiting toughness in the cured product. Further, when the cross-linkable silicon group is linked to the main chain via a polar group such as the nitrogen-containing characteristic group, the cross-linkable silicon groups are also close to each other while the nitrogen-containing characteristic groups form a domain with each other. Thereby, the contact probability between the cross-linkable silicon groups is also improved, and further, the condensation reactivity between the cross-linkable silicon groups is improved by the catalytic curing by the polar group in the nitrogen-containing characteristic group.

Such an organic polymer [A1] (modified silicone-based polymer) may be produced by a known method such as the method described in JPB198618569, or is commercially available. Commercially available products include, for example, Kaneka MS polymer series (MS polymer S203, MS polymer S303, MS polymer S903, MS polymer S911, MS polymer SAX520 etc.), Silyl series (Silyl polymer SAT200, Silyl polymer MA430, Silyl polymer MAX447 etc.), MA series, SA series, OR series available from Kaneka Corporation; ES series (ES-GX3440ST etc.), ESGX series etc. available from AGC Corporation.

The number average molecular weight of the organic polymer [A1] used in the present invention is not particularly limited. However, an excessively high molecular weight compound has a high viscosity, and when used as a curable composition, it becomes difficult to use the composition. Thus the number average molecular weight of the organic polymer [A1] is desirably 30,000 or less. Such an organic polymer may be produced by a known method, and a commercially available product such as the above-described Kaneka MS polymer available from Kaneka Corporation may be used.

(Organopolysiloxane [A2])

The organopolysiloxane [A2] used in the present invention has a main chain composed of a siloxane bond represented by Si—O, and further has an organic group bonded to a silicon atom constituting the siloxane bond. Specific examples of such organic groups include alkyl groups such as methyl, ethyl, propyl, and butyl; cycloalkyl groups such as cyclohexyl; alkenyl groups such as vinyl, isopropenyl, substituted vinyl; allyl groups, crotyl, substituted allyl groups such as methallyl; aryl groups such as phenyl, toluyl, and xylyl; aralkyl groups such as benzyl and phenylethyl; and groups in which all or part of the hydrogen atoms of these organic groups have been substituted with halogen atoms, such as a chloromethyl group and a 3,3,3-trifluoropropyl group.

Examples of the organopolysiloxane [A2] include those having a repeating unit represented by the following formula.

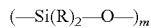

(In the formula, R represents the same or different organic groups, and m represents an integer of 2 or more.)

Specific examples include those having one or more kinds of repeating units such as

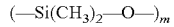

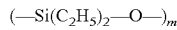

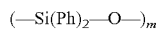

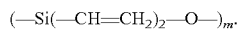

Here, m is the same or different and is an integer of 2 or more. The organopolysiloxane [A2] may be composed of a single main chain, or may be composed of two or more main chains.

The organopolysiloxane may be linear, and may be branched including trifunctional ($R'SiO_{1.5}$) or tetrafunctional ($SiO_2$). Further, depending on the physical properties and application of the cured product, a bifunctional form ($R'_2SiO$) or a monofunctional form ($R'_3SiO_{0.5}$) may be combined as necessary (where R' is an organic group). Further, the hydrolyzable silicon-containing group may be bonded to any of the molecular terminals and the middle of the molecular chain.

The organopolysiloxane is generally represented by an average composition formula of $R_aSiO_{4-a/2}$ (e.g., JPA2005194399 and JPA1996151521). The above notation followed this.

The viscosity of the organopolysiloxane [A2] used in the present invention is not particularly limited, but if the viscosity is excessively high, the workability may be reduced or the physical properties of the resulting cured product may be impaired. Thus the viscosity at 25° C. is desirably in the range of 0.025 to 100 Pa·s. Such an organopolysiloxane may be produced by a known method, and commercial products such as Tosseal series available from GE Toshiba Silicone Co., Ltd., Sealant series available from Shin-Etsu Chemical Co., Ltd., and SH series available from Toray Dow Corning Co., Ltd. may be used.

2. Curing Catalyst [B]

The curing catalyst [B] contains a metal alkoxide [B1] and a ammonium hydroxide [B2].

<Metal Alkoxide [B1]>

The metal alkoxide [B1] contains one or both of a titanium compound [B1a] and another metal alkoxide [B1b].

The titanium compound [B1a] is represented by Chemical Formula (1).

(In Chemical Formula (1), $R^1$ is a substituted or unsubstituted hydrocarbon group having 1 to 10 carbon atoms, n is an integer of 1 to 4 (that is 1,2,3, or 4), and A is a β-diketone group.)

The substituted or unsubstituted hydrocarbon group represented by $R^1$ is a substituted or unsubstituted aliphatic or aromatic hydrocarbon group, and an aliphatic hydrocarbon group is preferable. Examples of the aliphatic hydrocarbon group include saturated or unsaturated hydrocarbon groups. As the saturated hydrocarbon group, a linear or branched alkyl group is preferable. The number of carbon atoms in the hydrocarbon group is 1 to 10, preferably 1 to 6, and even more preferably 1 to 4. Specifically, the number of carbon atoms is, for example, 1, 2, 3, 4, 5, 6, 7, 8, 9, or 10, and may be within the range between any two of the numerical values exemplified here. Examples of the hydrocarbon group include methyl, ethyl, propyl, isopropyl, butyl, isobutyl, sec-butyl, tert-butyl, pentyl, hexyl, heptyl, octyl, 2-ethylhexyl, nonyl and decyl.

Examples of the β-diketone group represented by A include 2,4-pentandione, 2,4-hexanedione, 2,4-pentadecandione, 2,2,6,6-tetramethyl-3,5-heptanedione; 1-aryl-1,3-butandion such as 1-phenyl-1,3-butandione, 1-(4-methoxyphenyl)-1,3-butandione; 1,3-diaryl-1,3-propanedione such as 1,3-diphenyl-1,3-propanedione, 1,3-bis (2-pyridyl)-1,3-propanedione, 1,3-bis (4-methoxyphenyl)-1,3-propanedione; diketones such as 3-benzyl-2,4-pentandione; ketoesters such as methylacetate, ethylacetate, butylacetate, t-butylacetate, ethyl3-oxohexanoate; ketoamides such as N, N-dimethylacetacetamide, N, N-diethylacetacetamide, acetanilide; malonic acid esters such as dimethyl malonate, diethyl malonate, diphenyl malonate; malonic acid amides such as N, N, N', N'-tetramethylmalonamide, N, N, N', N'-tetraethylmalonamide. Diketones such as 2,4-pentandione, 1-aryl-1,3-butandione and 1,3-diaryl-1,3-propanedione are particularly preferred.

Specific examples of the titanium compound represented by Chemical Formula (1) include tetramethoxytitanium, trimethoxyethoxycititanium, trimethoxyisopropoxytitanium, trimethoxybutoxytitanium, dimethoxydiethoxytitanium, dimethoxydiisopropoxytitanium, dimethoxydibutoxytitanium, methoxytriethoxytitanium, methoxytriisopropoxytitanium, methoxytributoxytitanium, tetraethoxytitanium, triethoxyisopropoxytitanium, triethoxybutoxytitanium, diethoxydiisopropoxytitanium, diethoxydibutoxytitanium, ethoxytriisopropoxytitanium, ethoxytributoxytitanium, tetraisopropoxytitanium, triisopropoxybutoxytitanium, diisopropoxydibutoxytitanium, tetrabutoxytitanium, diisopropoxytitaniumbis(acetylacetonate) and the like.

From the viewpoint of catalytic activity, compound stability, and handleability, tetraisopropoxytitanium is more preferable.

The above-mentioned titanium compound [B1a] may be used alone or in combination of two or more kinds.

The another metal alkoxide [B1b] is an alkoxide of a metal other than titanium. Examples of the another metal alkoxide [B1b] include an alkoxide of a metal selected from aluminum, zirconium, zinc, sodium, potassium, lithium, magnesium and boron. The metal alkoxide contained in the another metal alkoxide [B1b] may be one kind or two or more kinds.

The alkoxy group of the another metal alkoxide [B1b] can be represented by Chemical Formula (3). The description of $R^6$ in Chemical Formula (3) is the same as that of $R^1$ in Chemical Formula (1). *Represents a binding site.

$$R^6—O—* \qquad (3)$$

When the another metal alkoxide [B1b] has a plurality of ligands, at least one of them is required to be an alkoxy group, and the rest may be other functional groups. Examples of other functional groups include a β-diketone group and a carboxyl group and the like. The description of the β-diketone group is the same as that of A in Chemical Formula (1).

Examples of the another metal alkoxide [B1b] include aluminum triisopropoxide, zirconium tetrapropoxide, zinc isopropoxide, sodium methylate, potassium methylate, lithium methylate, magnesium ethoxide, triethyl borate and the like.

The metal alkoxide [B1] may contain only the titanium compound [B1a], may contain only the another metal alkoxide [B1b], or may contain both of the titanium compound [B1a] and the another metal alkoxide [B1b].

The proportion of the titanium compound [B1a] in the metal alkoxide [B1] is, for example, 30 to 100% by mass, preferably 50 to 100% by mass. The proportion is, for example, 30, 40, 50, 60, 70, 80, 90, or 100% by mass, and may be in the range between any two of the numerical values exemplified here.

<Ammonium Hydroxide [B2]>

Ammonium hydroxide [B2] is represented by the following formula.

[Chem. 2]

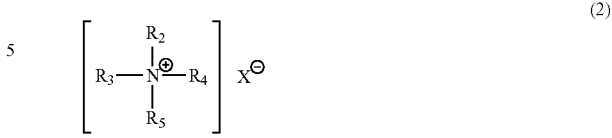

(In the formula, $R^2$, $R^3$, $R^4$ and $R^5$ represent substituted or unsubstituted hydrocarbon groups having 1 to 8 carbon atoms, which are the same as or different from each other. X represents a hydroxyl group.)

The substituted or unsubstituted hydrocarbon group represented by $R^2$, $R^3$, $R^4$, and $R^5$ is a substituted or unsubstituted aliphatic or aromatic hydrocarbon group, and an aliphatic hydrocarbon group is preferable. The aliphatic hydrocarbon group is preferably a linear or branched alkyl group. The number of carbon atoms of the hydrocarbon group is 1 to 8, preferably 1 to 6, and more preferably 1 to 4. Specifically, the number of carbon atoms is, for example, 1, 2, 3, 4, 5, 6, 7, or 8, and may be within the range between any two of the numerical values exemplified here. Examples of the aliphatic hydrocarbon group include saturated hydrocarbon groups such as a methyl group, an ethyl group, a propyl group, an isopropyl group, a butyl group, an isobutyl group, a pentyl group, a hexyl group, a cyclohexyl group, a heptyl group, an octyl group; unsaturated hydrocarbon groups such as a vinyl group, an allyl group, a prenyl group, a crotyl group, a cyclopentadienyl group, and the methyl group, the ethyl group and the butyl group are preferable.

Examples of the aromatic hydrocarbon group include a phenyl group, a tolyl group, a benzyl group and the like.

Examples of the substituent of the hydrocarbon group include a methoxy group, an ethoxy group, a hydroxy group, an acetoxy group and the like. Examples of the substituted aliphatic or aromatic hydrocarbon group include alkoxyalkyl groups such as a methoxymethyl group, methoxyethyl group, ethoxymethyl group and ethoxyethyl group; hydroxyalkyl groups such as hydroxymethyl group, hydroxyethyl group and 3-hydroxypropyl group, 2-acetoxyethyl group and the like.

Examples of the ammonium hydroxide represented by Chemical Formula (2) include tetramethylammonium hydroxide, tetraethylammonium hydroxide, tetrapropylammonium hydroxide, trimethylbenzylammonium hydroxide, benzyltriethylammonium hydroxide, trimethylphenylammonium hydroxide, tris (2-hydroxyethyl) methylammonium hydroxide and the like, and the tetramethylammonium hydroxide is particularly preferable.

The content ratio (B1/B2) of the metal alkoxide [B1] and the ammonium hydroxide [B2] is in the range of 0.1/1 to 10/1 in terms of molar ratios. From the viewpoint of obtaining good curability, 1/1 to 10/1 is preferable, and 2/1 to 5/1 is more preferable.

3. Moisture-Curable Composition

The moisture-curable composition of the present invention contains the above-mentioned curing catalyst [B] and the polymer [A], and may further contain other additives as described below as necessary. The preparation of the moisture-curable composition of the present invention may be performed by mixing both under dry conditions, and the form of mixing is not particularly limited. Usually, the mixing may be carried out in an atmosphere at a temperature of about 15 to 30° C. and 60% RH or less.

In the moisture-curable composition of the present invention, a content of the curing catalyst [B] is preferably 0.1 to 20 parts by weight with respect to 100 parts by weight of the polymer [A], more preferably 0.5 to 10 parts by weight, particularly preferably 3 to 8 parts by weight. If the content of the curing catalyst [B] is less than 0.1 part by weight, the curing performance may be insufficient, and if the content of the curing catalyst [B] exceeds 20 parts by weight, the cured product after curing may have poor recovery rate, physical properties such as weather resistance, and stability during storage. Specifically, the content of the curing catalyst [B] is, for example, 0.1, 0.5, 1, 2, 3, 4, 5, 6, 7, 8, 9, 10, 11, 12, 13, 14, 15, 16, 17, 18, 19, 20 parts by weight with respect to 100 parts by weight of the polymer [A], and may be within the range between any two of the numerical values exemplified here.

The moisture-curable composition of the present invention may further contain a filler [C]. Examples of the filler include calcium carbonate, kaolin, talc, fumed silica, precipitated silica, silicic anhydride, hydrous silicic acid, clay, calcined clay, glass, bentonite, organic bentonite, shirasu balloon, glass fiber, asbestos, glass filament, crushed quartz, diatomaceous earth, aluminum silicate, aluminum hydroxide, zinc oxide, magnesium oxide, titanium dioxide and the like. The filler may be used alone or in combination of two or more kinds. By adding the filler, the handling of the moisture-curable composition is improved. The filler also acts as a rubber reinforcing agent for the cured product. The greatest advantage is that the amount of resin used can be reduced by adding the filler as an extender, so that the cost can be reduced.

Among the fillers described above, calcium carbonate and titanium dioxide are preferred from the viewpoint of maintaining excellent non-tack surface, 50% modulus, workability, weather resistance and the like of the cured curable composition. When calcium carbonate is used, the proportion is preferably 1 to 200, more preferably 50 to 200 parts by weight with respect to 100 parts by weight of the polymer [A]. When it is in the above range, the properties after curing are not impaired.

The moisture-curable composition of the present invention may further contain additives usually added to the curable composition, such as other curing catalysts, a curing accelerator, a coloring agent, a plasticizer, a curing retarder, an anti-sagging agent, an anti-aging agent, and a solvent.

Examples of other curing catalysts include Metal curing catalysts such as organotin compounds such as dibutyltin dilaurate, dibutyltin bis (acetylacetone), organoaluminium compounds such as aluminum tris (acetylacetonate) and aluminum tris (ethylacetacetate), organozirconium compounds such as zirconium tetra (acetylacetonate) and zirconium tetrabutyrate; amine compounds such as 1-amino-2-ethylhexane, 3-(trimethoxysilyl) propylamine, N-2-aminoethyl-3-aminopropyltrimethoxysilane, N, N, N', N'-tetramethyl-N''-[3-(trimethoxysilyl) propyl] guanidine, 1,5,7-triazabicyclo-[4,4,0] deca-5-ene, 3-triethoxysilyl-N-(1,3-dimethylbutylidene) propylamine and the like.

As the curing accelerator, for example, various known amino group-substituted alkoxysilane compounds or condensates thereof can be used. Specific examples of the curing accelerator include γ-aminopropyltrimethoxysilane, γ-aminopropyltriethoxysilane, N-(trimethoxysilylpropyl) ethylenediamine, δ-aminobutyl (methyl) diethoxysilane, N,N-bis (trimethoxysilylpropyl) ethylenediamine and partial hydrolysate thereof. These curing accelerators also have the effect of improving the adhesion to the substrate.

Specific examples of the coloring agent include iron oxide, carbon black, phthalocyanine blue, phthalocyanine green and the like.

Specific examples of the plasticizer include phthalates such as dibutyl phthalate, dioctyl phthalate and butylbenzyl phthalate; aliphatic carboxylic acid esters such as dioctyl adipate, dioctyl succinate, diisodecyl succinate, butyl oleate; glycol esters such as pentaerythritol esters; phosphates such as trioctyl phosphate and tricresyl phosphate; epoxy plasticizers such as epoxidized soybean oil and benzyl epoxy stearate; chlorinated paraffins and the like.

Specific examples of the anti-sagging agent include hydrogenated castor oil, silicic anhydride, organic bentonite, colloidal silica and the like.

Further, as other additives, adhesion imparting agents such as a phenol resin and an epoxy resin, an ultraviolet absorber, a radical chain inhibitor, a peroxide decomposer, various anti-aging agents and the like may be used.

The curable composition of the present invention is sufficiently stable at room temperature and thus has excellent storage properties, and the curing reaction proceeds spontaneously when it is brought into contact with moisture due to the blended curing catalyst [B]. In addition, the snap time (the time until the gel is semi-gelled and the fluidity disappeared) and the tack-free time (the time until the surface tack disappeared) are short and workability is excellent.

According to the above characteristics, the curable composition of the present invention can be used as a one-pack type sealing material. Specifically, it is suitably used for applications such as sealing materials, adhesives, sealants, waterproof fillers for buildings, ships, and vehicles such as automobiles.

EXAMPLES

Hereinafter, the present invention will be specifically described with reference to examples, but the scope of the present invention is not limited thereto.

Production Example 1 (Diacetylacetonatotitanium Diisopropoxide)

71.1 g (0.25 mol) of tetraisopropoxytitanium was charged into a 500 mL 4-neck round-bottom flask equipped with a nitrogen inlet tube. While agitating, 50.0 g (0.50 mol) of 2,4-pentandione was added in a dropwise manner over 30 minutes at an internal temperature of 20 to 50° C., heated in an oil bath to maintain an internal temperature of 87 to 90° C., and then agitated as it was for 1 hour. Then, concentration under reduced pressure (final decompression degree: 14 mmHg) was performed to distill off isopropanol. 30 g of distillate and 91 g of red concentrated titanium complex were obtained in a 500 mL round bottom flask.

Comparative Production Example 1 (Titanium Isopropoxide Acetate)

200.00 g (0.70368 mol) of tetraisopropoxytitanium and 42.2 g (0.703681 mol) of acetic acid were weighed into a 1000 mL 4-necked eggplant-shaped flask equipped with a nitrogen inlet tube, and thoroughly mixed with an agitator. Agitation of the mixture is continued until the internal temperature reached around 110° C., and then isopropyl alcohol was distilled off under reduced pressure. 196 g (98%) of titanium isopropoxide acetate was obtained as a yellow liquid.

Comparative Production Example 2
(Tetrabutylammonium Octylate)

70 g (0.1 mol) of 37% tetrabutylammonium hydroxide methanol solution and 14.2 g (0.1 mol) of octyl acid were weighed into a 100 mL 4-necked eggplant-shaped flask equipped with a nitrogen inlet tube, and thoroughly mixed with an agitator. Methanol was distilled off by concentration under reduced pressure. 80 g of tetrabutylammonium octylate was obtained as a colorless liquid.

(Preparation of Moisture-Curable Composition)

Each component obtained in the above production examples and a commercially available component were blended at the blending ratios (parts by mass) shown in Tables 1 and 2, and kneaded to prepare a moisture-curable composition. The mass of each component of the curing catalyst [B] in the tables indicates the amount of the active ingredient. Therefore, for example, in "10% lithium methylate", the concentration of lithium methylate is 10% by mass, so that the amount of "10% lithium methylate" added is 10 times the value in the tables. The operations up to blending, kneading and curing were performed in an atmosphere of 25±1° C. and 50-60% RH.

<Measurement of Tack-Free Time>

The tack-free time of the obtained moisture-curable composition was measured. The tack-free time is a time required from the end of kneading until the sample no longer adheres to the fingertip after lightly touching three places on the surface with a fingertip cleaned with ethyl alcohol. The results of the tack-free time measurement are shown in Tables 1 and 2.

TABLE 1

| | | | | Examples | | | | | | | |
| --- | --- | --- | --- | --- | --- | --- | --- | --- | --- | --- | --- |
| | | | | 1 | 2 | 3 | 4 | 5 | 6 | 7 | 8 |
| Polymer [A] | [A1] | | MS Polymer SAX520 | 100 | 100 | 100 | 100 | 100 | 100 | 100 | 100 |
| Curing Catalyst [B] | [B1] | [B1a] | Tetraisopropoxytitanium | 3.0 | 2.0 | | 3.0 | 3.0 | 3.0 | 3.0 | 3.0 |
| | | [B1a] | Diacetylacetonatotitanium Diisopropoxide | | | 2.0 | | | | | |
| | | [B1b] | Aluminum Triisopropoxide | | | | 1.0 | | | | |
| | | [B1b] | Zirconium Tetrapropoxide | | | | | 1.0 | | | |
| | | [B1b] | Zinc Diisopropoxide | | | | | | 1.0 | | |
| | | [B1b] | Sodium Methylate | | | | | | | 1.0 | |
| | | [B1b] | Potassium methylate | | | | | | | | 1.0 |
| | [B2] | | Tetrabutylammonium Hydroxide | 1.0 | 2.0 | 2.0 | 1.0 | 1.0 | 1.0 | 1.0 | 1.0 |
| Filler | Calcium Carbonate | | CAREX 300 | 122 | 122 | 122 | 122 | 122 | 122 | 122 | 122 |
| | Titanium Oxide | | FR-41 | 20 | 20 | 20 | 20 | 20 | 20 | 20 | 20 |
| Other Additives | Plasticizer | | DINP | 42 | 42 | 42 | 42 | 42 | 42 | 42 | 42 |
| | Anti-Sagging Agent | | DISPARLON 6500 | 1.0 | 1.0 | 1.0 | 1.0 | 1.0 | 1.0 | 1.0 | 1.0 |
| | Ultraviolet Absorber | | Songsorb 3260P | 1.0 | 1.0 | 1.0 | 1.0 | 1.0 | 1.0 | 1.0 | 1.0 |
| | Light Stabilizer | | Sabostab UV70 | 1.0 | 1.0 | 1.0 | 1.0 | 1.0 | 1.0 | 1.0 | 1.0 |
| | Antioxidant | | Irganox245 | 1.0 | 1.0 | 1.0 | 1.0 | 1.0 | 1.0 | 1.0 | 1.0 |
| | Dehydrating Agent | | KBM-1003 | 2.3 | 2.3 | 2.3 | 2.3 | 2.3 | 2.3 | 2.3 | 2.3 |
| | Adhesion Imparting Agent | | KBM-603 | 3.2 | 3.2 | 3.2 | 3.2 | 3.2 | 3.2 | 3.2 | 3.2 |
| Tack-Free Time | | | | 5 min | 50 min | 80 min | 5 min | 5 min | 5 min | 5 min | 5 min |

TABLE 2

| | | | | Examples | | | Comparative Examples | | | | |
| --- | --- | --- | --- | --- | --- | --- | --- | --- | --- | --- | --- |
| | | | | 9 | 10 | 11 | 1 | 2 | 3 | 4 | 5 |
| Polymer [A] | [A1] | | MS Polymer SAX520 | 100 | 100 | 100 | 100 | 100 | 100 | 100 | 100 |
| Curing Catalyst [B] | [B1] | [B1a] | Tetraisopropoxytitanium | 3.0 | 3.0 | 3.0 | 4.0 | | | | 2.0 |
| | | [B1a] | Diacetylacetonatotitanium Diisopropoxide | | | | | | 4.0 | | |
| | | [B1b] | Lithium Methylate | 1.0 | | | | | | | |
| | | [B1b] | Magnesium Ethoxide | | 1.0 | | | | | | |
| | | [B1b] | Triethyl Borate | | | 1.0 | | | | | |
| | [B2] | | Tetrabutylammonium Hydroxide | 1.0 | 1.0 | 1.0 | | 4.0 | | 2.0 | |
| Other Catalysts | Metal Alkoxide Other Than [B1] | | Titanium isopropoxide Acetate | | | | | | | 2.0 | |
| | Quaternary Ammonium Salt Other Than [B2] | | Tetrabutylammonium Octylate | | | | | | | | 2.0 |
| Filler | Calcium Carbonate | | CAREX 300 | 122 | 122 | 122 | 122 | 122 | 122 | 122 | 122 |
| | Titanium Oxide | | FR-41 | 20 | 20 | 20 | 20 | 20 | 20 | 20 | 20 |
| Other Additives | Plasticizer | | DINP | 42 | 42 | 42 | 42 | 42 | 42 | 42 | 42 |
| | Anti-Sagging Agent | | DISPARLON 6500 | 1.0 | 1.0 | 1.0 | 1.0 | 1.0 | 1.0 | 1.0 | 1.0 |
| | Ultraviolet Absorber | | Songsorb 3260P | 1.0 | 1.0 | 1.0 | 1.0 | 1.0 | 1.0 | 1.0 | 1.0 |
| | Light Stabilizer | | Sabostab UV70 | 1.0 | 1.0 | 1.0 | 1.0 | 1.0 | 1.0 | 1.0 | 1.0 |
| | Antioxidant | | Irganox245 | 1.0 | 1.0 | 1.0 | 1.0 | 1.0 | 1.0 | 1.0 | 1.0 |
| | Dehydrating Agent | | KBM-1003 | 2.3 | 2.3 | 2.3 | 2.3 | 2.3 | 2.3 | 2.3 | 2.3 |
| | Adhesion Imparting Agent | | KBM-603 | 3.2 | 3.2 | 3.2 | 3.2 | 3.2 | 3.2 | 3.2 | 3.2 |
| Tack-Free Time | | | | 5 min | 5 min | 5 min | 4 h | 3 h | 5 h | >10 h | >10 h |

As shown in Examples 1 to 3 and Comparative Examples 1 to 3, a remarkable improvement in activity is observed when the metal alkoxide [B1] and the ammonium hydroxide [B2] are used in combination as compared with the case of each alone. In particular, in Examples 1 to 4 and 6 to 7, the non-tin catalyst has a very high activity and can be sufficiently used for sealing and adhesive applications.

Further, as shown in Comparative Example 4, the activity is low in the combination of the metal alkoxide other than the metal alkoxide [B1] and the ammonium hydroxide [B2]. Furthermore, as shown in Comparative Example 5, the activity is also low when the metal alkoxide [B1] and a quaternary ammonium salt other than the ammonium hydroxide [B2] are used in combination.

The details of the materials shown in Tables 1 to 2 are as follows.

(Polymer [A])
MS Polymer SAX520: silyl group-containing organic polymer (Kaneka Co., Ltd.)
(Curing Catalyst [B])
Tetraisopropoxytitanium: available from Tokyo Chemical Industry Co., Ltd.
Diacetylacetonatotitanium diisopropoxide: manufactured in Production Example 1
Aluminum triisopropoxide: available from Tokyo Chemical Industry Co., Ltd.
Zirconium tetrapropoxide: available from Tokyo Chemical Industry Co., Ltd.
Zinc diisopropoxide: available from Wako Pure Chemical Industries, Ltd.
Sodium methylate: 28% Sodium methylate; available from Wako Pure Chemical Industries, Ltd.
Potassium methylate: 30% Potassium methylate; available from Wako Pure Chemical Industries, Ltd.
Lithium methylate: 10% Lithium methylate; available from Wako Pure Chemical Industries, Ltd.
Magnesium ethoxide: available from Tokyo Chemical Industry Co., Ltd.
Triethyl borate: available from Tokyo Chemical Industry Co., Ltd.
Tetrabutylammonium hydroxide: 37% Tetrabutylammonium hydroxide; available from Tokyo Chemical Industry Co., Ltd.
(Other Catalysts)
Titanium isopropoxide acetate: manufactured in Comparative Production Example 1
Tetrabutylammonium octylate: manufactured in Comparative Production Example 2
(Filler)
CAREX 300: calcium carbonate (Maruo Calcium Co., Ltd.)
FR-41: titanium oxide (Furukawa Chemicals Co., Ltd.)
(Other Additives)
DINP: plasticizer (J-PLUS Co., Ltd.)
DISPARLON 6500: anti-sagging agent (Kusumoto Chemicals Co., Ltd.)
Songsorb 3260P: ultraviolet absorber (SONGWON)
Sabostab UV-70: light stabilizer (SONGWON)
Irganox 245: antioxidant (BASF Japan Ltd.)
KBE-1003: dehydrating agent (Shin-Etsu Silicone Industry Co., Ltd.)
KBM-603: adhesion imparting agent (Shin-Etsu Silicone Industry Co., Ltd.)

The invention claimed is:

1. A curing catalyst [B] used for curing a polymer [A] having a reactive hydrolyzable silicon-containing group, wherein the curing catalyst [B] contains a metal alkoxide [B1] and an ammonium hydroxide [B2],
the metal alkoxide [B1] contains both a titanium compound [B1a] represented by Chemical Formula (1) and another metal alkoxide [B1b],
the another metal alkoxide [B1b] is an alkoxide of a metal other than titanium,
the ammonium hydroxide [B2] is represented by Chemical Formula (2),

$$(R^1-O)_n\text{Ti-A}_{4-n} \quad (1)$$

in Chemical Formula (1), $R^1$ is a substituted or unsubstituted hydrocarbon group having 1 to 10 carbon atoms, n is an integer of 1 to 4, and A is a β-diketone group,

[Chem. 2]

$$\left[\begin{array}{c} R_2 \\ | \\ R_3-\overset{\oplus}{N}-R_4 \\ | \\ R_5 \end{array}\right] X^{\ominus} \quad (2)$$

in Chemical Formula (2), $R^2$, $R^3$, $R^4$ and $R^5$ represent substituted or unsubstituted hydrocarbon groups having 1 to 8 carbon atoms, which are the same as or different from each other, and X represents a hydroxy group.

2. The curing catalyst [B] of claim 1, wherein the metal alkoxide [B1] contains the titanium compound [B1a].

3. The curing catalyst [B] of claim 1, wherein the another metal alkoxide [B1b] is an alkoxide of a metal selected from aluminum, zirconium, zinc, sodium, potassium, lithium, magnesium and boron.

4. A moisture-curable composition comprising a curing catalyst [B] and a polymer [A] having a reactive hydrolyzable silicon-containing group, wherein
the curing catalyst [B] contains a metal alkoxide [B1] and an ammonium hydroxide [B2],
the metal alkoxide [B1] contains one or both of a titanium compound [B1a] represented by Chemical Formula (1) and another metal alkoxide [B1b],
the another metal alkoxide [B1b] is an alkoxide of a metal other than titanium,
the ammonium hydroxide [B2] is represented by Chemical Formula (2),

$$(R^1-O)_n\text{Ti-A}_{4-n} \quad (1)$$

in Chemical Formula (1), $R^1$ is a substituted or unsubstituted hydrocarbon group having 1 to 10 carbon atoms, n is an integer of 1 to 4, and A is a β-diketone group,

[Chem. 2]

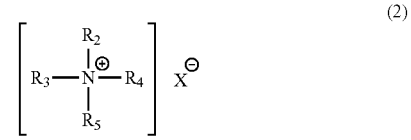

$$\left[\begin{array}{c} R_2 \\ | \\ R_3-\overset{\oplus}{N}-R_4 \\ | \\ R_5 \end{array}\right] X^{\ominus} \quad (2)$$

in Chemical Formula (2), $R^2$, $R^3$, $R^4$ and $R^5$ represent substituted or unsubstituted hydrocarbon groups having 1 to 8 carbon atoms, which are the same as or different from each other, and X represents a hydroxy group.

5. A method for producing a cured product, comprising a step of bringing the moisture-curable composition of claim 4 into contact with moisture.

6. The moisture-curable composition of claim 4, wherein the metal alkoxide [B1] contains the titanium compound [B1a] and the another metal alkoxide [B1b].

* * * * *